(12) United States Patent
French et al.

(10) Patent No.: US 6,467,282 B1
(45) Date of Patent: Oct. 22, 2002

(54) FROST SENSOR FOR USE IN DEFROST CONTROLS FOR REFRIGERATION

(76) Inventors: Patrick D. French, ADA Technologies, Inc. 8100 Shaffer Pkwy., Suite 130, Littleton, CO (US) 80127-4107; James R. Butz, ADA Technologies, Inc. 8100 Shaffer Pkwy., Suite 130, Littleton, CO (US) 80127-4107; Bradley D. Veatch, ADA Technologies, Inc. 8100 Shaffer Pkwy., Suite 130, Littleton, CO (US) 80127-4107; Michael W. O'Connor, ADA Technologies, Inc. 8100 Shaffer Pkwy., Suite 130, Littleton, CO (US) 80127-4107

( * ) Notice: Subject to any disclaimer, the term of this patent is extended or adjusted under 35 U.S.C. 154(b) by 0 days.

(21) Appl. No.: 09/957,169

(22) Filed: Sep. 18, 2001

Related U.S. Application Data
(60) Provisional application No. 60/236,022, filed on Sep. 27, 2000, and provisional application No. 60/270,748, filed on Feb. 21, 2001.

(51) Int. Cl.$^7$ .............................................. F25D 21/06
(52) U.S. Cl. .......................................... 62/140; 62/151
(58) Field of Search .......................... 62/140, 151, 156, 62/171, 180, 259.4, 305; 165/104.33; 374/29, 30

(56) References Cited

U.S. PATENT DOCUMENTS

| | | | |
|---|---|---|---|
| 3,525,648 A | 8/1970 | Poppendiek | |
| 3,854,915 A | 12/1974 | Schulze-Berge et al. | |
| 3,945,217 A | 3/1976 | Bashark | |
| 4,037,427 A | * 7/1977 | Kramer | 62/128 |
| 4,045,971 A | * 9/1977 | Brenner et al. | 62/140 |
| 4,142,374 A | 3/1979 | Ansted et al. | |
| 4,156,350 A | 5/1979 | Elliott et al. | |
| 4,173,871 A | 11/1979 | Brooks | |
| 4,305,259 A | 12/1981 | Jaeschke | |
| 4,329,682 A | 5/1982 | Baker | |
| 4,344,294 A | 8/1982 | Gelbard | |
| 4,345,441 A | 8/1982 | Hansen | |
| 4,347,709 A | 9/1982 | Wu et al. | |
| 4,348,870 A | 9/1982 | Stein et al. | |
| 4,409,795 A | 10/1983 | Krueger | |
| 4,481,785 A | 11/1984 | Tershak et al. | |
| 4,528,821 A | 7/1985 | Tershak et al. | |
| 4,530,218 A | 7/1985 | Janke et al. | |
| 4,532,806 A | 8/1985 | Bruchmuller | |

(List continued on next page.)

OTHER PUBLICATIONS

Eckman, R. L., "Heat Pump Defrost Controls: A Review of Past, Present and Future Technology" presented at the 1987 Winter Meeting of ASHRAE and published in the ASHRAE Transactions: Technical and Symposium Papers for that conference, (1987), pp. 1152–1156.

(List continued on next page.)

*Primary Examiner*—Denise L. Esquivel
*Assistant Examiner*—Marc Norman
(74) *Attorney, Agent, or Firm*—Robert M Hunter

(57) ABSTRACT

An apparatus and method for measuring the total thermal resistance to heat flow from the air to the evaporative cooler fins of a refrigeration system. The apparatus is a frost sensor that measures the reduction in heat flow due to the added thermal resistance of ice (reduced conduction) as well as the reduction in heat flow due to the blockage of airflow (reduced convection) from excessive ice formation. The sensor triggers a defrost cycle when needed, instead of on a timed interval. The invention is also a method for control of frost in a system that transfers heat from air to a refrigerant along a thermal path. The method involves measuring the thermal conductivity of the thermal path from the air to the refrigerant, recognizing a reduction in thermal conductivity due to the thermal insulation effect of the frost and due to the loss of airflow from excessive ice formation; and controlling the defrosting of the system.

28 Claims, 7 Drawing Sheets

U.S. PATENT DOCUMENTS

| | | | |
|---|---|---|---|
| 4,608,832 | A | 9/1986 | Sabin et al. |
| 4,671,072 | A | 6/1987 | Starck et al. |
| 4,882,908 | A | 11/1989 | White |
| 4,993,233 | A | 2/1991 | Borton et al. |
| 5,051,645 | A | 9/1991 | Brace et al. |
| 5,319,943 | A | 6/1994 | Bahel et al. |
| 5,345,775 | A | 9/1994 | Ridenour |
| 5,493,867 | A | 2/1996 | Svnal et al. |
| 5,522,232 | A | 6/1996 | Nojiri |
| 5,692,385 | A | 12/1997 | Hollenbeck et al. |
| 6,038,872 | A | 3/2000 | Nojiri |
| 6,092,925 | A | 7/2000 | Nojiri |
| 6,112,534 | A * | 9/2000 | Taras et al. .............. 62/217 |

OTHER PUBLICATIONS

Heinzen, R. A., "How Adaptive Defrost Maintains Refrigeration System Efficiency" in Australian Refrigeration, Air Conditioning and Heating, (Apr. 1988), pp. 12–16, 42–4.

Paone, N. et al., "Fiber–optic ice sensors for refrigerators" in SPIE Fiber–Optic Sensors: Engineering and Applications, (Mar., 1991), pp. 129–130, 1511.

Energetics, Inc., Refrigeration Systems Program Summary, DOE/CH/10093 120, (Dec., 1991), pp. 1–8, U.S. Department of Energy, Washington, D.C.

Borton, D.N. et al., Development of a Demand Defrost Controller, (Oct., 1993), pp. i through 4–7, New York State Energy Research and Development Authority, Albany, New York.

Westphalen D. et al., Energy Savings Potential for Commercial Refrigeration Equipment—Final Report, (Jun., 1996), pp. i through 3–3, U.S. Department of Energy, Office of Building Technologies, Washington, D.C.

Office of Industrial Technologies, U.S. Department of Energy, Energy Saving Intelligent Contoller for Refrigeration (Nov., 2000), pp. 1–2, U.S. Department of Energy, Office of Industrial Technologies, Washington, D.C.

Stoecker, W. F. et al., "Energy Considerations in Hot–Gas Defrosting of Industrial Refrigeration Coils," Report No. 2796, ASHRAE Project RP–193, in Energy Consideration in Hot–Gas Defrosting of Industrial Refrigeration Coils, presented at the 1983 Annual Meeting of ASHRAE and published in the ASHRAE Transactions; Technical and Symposium Papers for that conference, (1983), pp. 549–573.

* cited by examiner

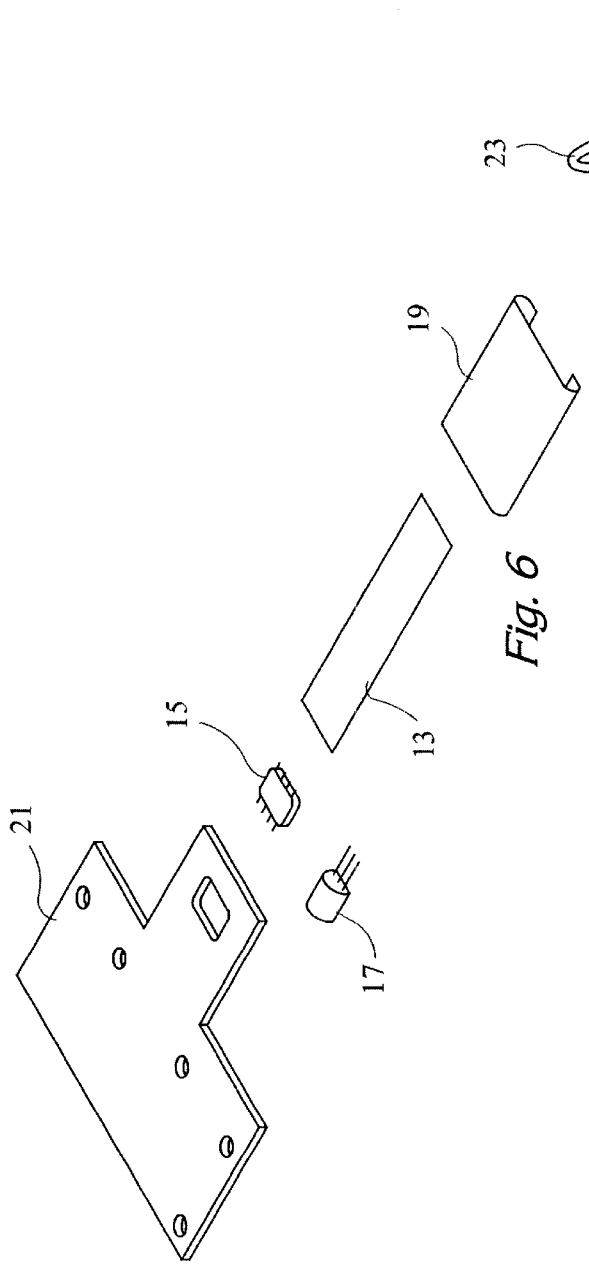
Fig. 6
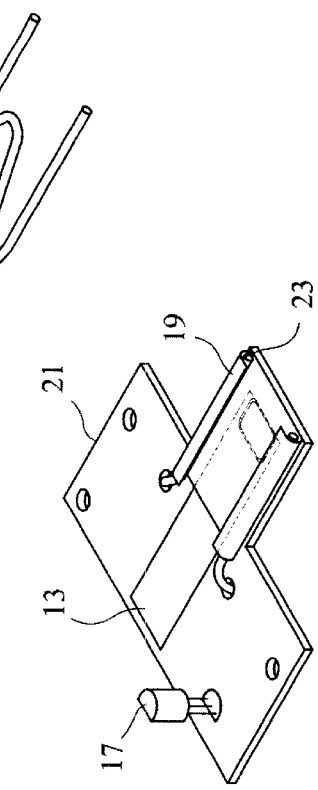
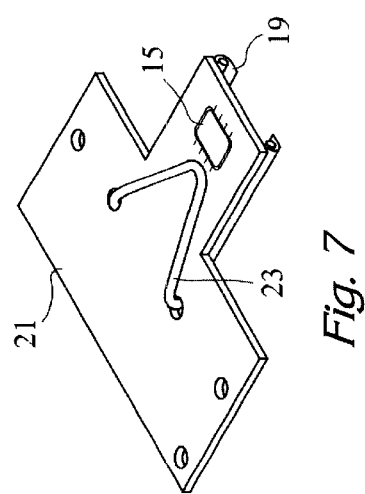
Fig. 7
Fig. 8

FROST SENSOR FOR USE IN DEFROST CONTROLS FOR REFRIGERATION

CROSS-REFERENCE TO RELATED APPLICATIONS

This application claims the benefit of U.S. Provisional Application No. 60/236,022, filed Sep. 27, 2000, and U.S. Provisional Application No. 60/270,748, filed on Feb. 21, 2001, the disclosures of which applications are incorporated by reference as if fully set forth herein.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. DE-FG03-97ER82309 awarded by the U.S. Department of Energy.

BACKGROUND OF THE INVENTION

This invention relates to a frost sensor for use in defrost controls for refrigeration and a system that incorporates the frost sensor. In particular, the invention relates to an apparatus and method for sensing the buildup of insulating accumulations or materials (e.g., ice or dirt) on the evaporative heat exchanger of a refrigeration system and for controlling the operation of the system.

The evaporative coils of commercial and industrial refrigeration systems form frost because the evaporative coil surface is below freezing and warmer moist air is blown across the coil in order to cool the refrigerated space. This frost deposition accumulates over time to form ice deposits that reduce the efficiency of the refrigeration system. The efficiency is reduced because the ice acts as a thermal insulator of the cooling coil and also blocks airflow over the cooling fins of the coil. It is therefore necessary to defrost the evaporative coils periodically in order to maintain cooling capacity. Current defrost controls are predominantly time clocks which are typically set to defrost too often and for too long a period.

Significant power savings can be realized by defrosting the heat-exchanger in refrigeration systems only when necessary, and only for as long as necessary. On the order of 5 percent to 12 percent of the total power consumed in refrigeration can be saved by the proper implementation of a demand-defrost system. For a commercial system to be successful, it must: (1) use a rugged sensor (having a longer life than the refrigeration unit, with zero maintenance), (2) have universal application to different heat-exchangers, (3) add no complexity to system operation, and (4) be low-cost in terms of hardware and installation. A variety of types of demand-defrost systems have been proposed.

Optically-based sensors have been installed to detect frost buildup. When frost reaches a preset thickness, a defrost cycle is initiated. Several sensors of this type have been marketed with limited success, primarily because the sensors trigger unnecessary defrosts due to dirty environments and require intensive maintenance. Because sensors have to be located at the display-case evaporator, replacement of a failed sensor is very difficult, often requiring removal of refrigerated product from the case. For this reason, failed sensors are generally replaced with standard timers.

A temperature-sensor-based demand-defrost controller was developed and introduced by Honeywell. The controller employed two temperature sensors located at the inlet and outlet of the display case evaporator. Defrost was initiated when the temperature difference between the two sensors reached a defined setpoint. This controller did not gain wide acceptance because it was prone to triggering defrosts unnecessarily.

A system that was developed but was never made commercially available used the temperature difference between the inlet to the heat-exchanger fan and the air temperature after blowing over the heat-exchanger. Application of this system was limited to systems with specific hardware configurations. Identifying the actual trigger point for defrosting for most systems added too much complexity for the average operator. In addition, the formation of ice on the heat-exchanger blocked much of the air flow and thereby produced a lower flow of air that still had a large enough temperature drop so that defrost was not initiated even after the heat-exchanger frosted.

Pressure-sensor technology measures the change in refrigerant pressure through the evaporator as frost is deposited on the surface and can signal when defrost is required. The magnitude of this pressure difference is very small (a fraction of an inch of water) which is difficult to measure accurately. Moreover, the cost of accurate pressure sensors is prohibitively high, which makes them unattractive for defrost control.

A number of systems that rely on some type of adaptive control have been proposed, with a moderate degree of technical success. These systems were commercial failures because of the complexity of troubleshooting. Since the triggering is not based on a simple, single measurement, the operators cannot easily identify the problem. In virtually all cases, the system is immediately bypassed, reverting back to timing clocks. As a practical matter, once a system has been bypassed, it is seldom repaired.

The background art is characterized by U.S. Pat. Nos. 3,525,648; 3,854,915; 3,945,217; 4,142,374; 4,156,350; 4,173,871; 4,305,259; 4,329,682; 4,344,294; 4,345,441; 4,347,709; 4,348,870; 4,409,795; 4,481,785; 4,528,821; 4,530,218; 4,532,806; 4,608,832; 4,671,072; 4,882,908; 4,993,233; 5,051,645; 5,319,943; 5,345,775; 5,493,867; 5,522,232; 5,692,385; 6,038,872; and 6,092,925; the disclosures of which patents are incorporated by reference as if fully set forth herein.

Poppendiek in U.S. Pat. No. 3,525,648 discloses a thermoelectric heat flow responsive device. An embodiment of this device is incorporated into the invention of U.S. Pat. No. 4,608,832, discussed below. This device is limited in that it appears to be relatively thick, possibly over ⅙ inch in thickness. Moreover, the device has a substantial resistance to heat flow due to the relatively high number of interfaces between the layers that make up the device and due to the thickness of the device. This suggests that a temperature drop of several degrees would occur across the device. This substantial resistance limits the applications of the device to other than frost sensing in a refrigeration system. If the air-exposed side of a heat flux sensor is several degrees warmer than the adjacent fin surface, ice will preferentially form on the fin and not on the heat flux sensor, rendering a defrost control system that incorporates such a heat flux sensor inoperative.

Schulze-Berge et al. in U.S. Pat. No. 3,854,915 disclose a demand defrost system. This invention is limited in that a periodic switch device is required to initiate defrost cycles in response to relative humidity values ambient to a refrigeration system.

Barshark in U.S. Pat. No. 3,945,217 discloses a refrigeration system defrost control. This invention is limited in that it includes a sensor that exhibits a change in resistance as a function of the amount of moisture it absorbs. When the sensor has absorbed a certain amount of water, a defrost cycle is initiated. The sensor must be dried during the defrost cycle.

Ansted et al. in U.S. Pat. No. 4,142,374 disclose a demand defrost time clock control circuit. This invention is limited in that the construction and method of operation of its frost sensor appears to be a conventional optical frost sensor, preferably produced by Altech, Inc.

Elliott et al. in U.S. Pat. No. 4,156,350 disclose a demand defrost control system and method. This invention is limited in that it bases the interval between future defrosting operations on the time required for the defrost heater to raise the evaporator temperature to a predetermined temperature during a previous defrosting operation.

Brooks in U.S. Pat. No. 4,173,871 discloses a demand defrost control system and method. This invention is limited in that it bases the interval between future defrosting operations on the time required for the defrost heater to raise the evaporator temperature to a predetermined temperature during a previous defrosting operation.

Jaeschke in U.S. Pat. No. 4,305,259 discloses a frost sensor employing a self-heating thermistor as a sensor element. This invention is limited in that current must be applied to the thermistor to cause it to increase in temperature during a frost measurement.

Baker in U.S. Pat. No. 4,329,682 discloses a method and apparatus for providing a warning of icing conditions in an aircraft air conditioning system. This invention is limited in that a thermo-electric heat pump is used to maintain a constant difference between the temperature of a cold surface in an air stream and temperature of the air stream.

Gelbard in U.S. Pat. No. 4,344,294 discloses a thermal delay demand defrost system. This invention is limited in that it requires that sensing of the temperature of the refrigerated air be used to alter the duration of time between defrost cycles.

Hansen in U.S. Pat. No. 4,345,441 discloses a defrost control apparatus for the evaporator of a refrigerator. This invention is limited in that it requires that a temperature sensor be mounted a predetermined distance from a surface of the evaporator. Defrosting occurs when the sensor temperature falls below a reference temperature.

Wu et al. in U.S. Pat. No. 4,347,709 disclose a demand defrost sensor. This invention is limited in that it requires that a capacitive sensor plate be installed next to the evaporator surface and that a noise-immune phase detector be used to detect a phase shift caused by frost buildup.

Stein et al. in U.S. Pat. No. 4,348,870 disclose a temperature probe for an air conditioning device. The device is limited in that it includes a freeze-up thermistor that is used to sense the temperature within an evaporator tube array. The sensor produces a signal that is indicative of freeze-up or insipient freeze-up, which signal is used to terminate the operation of the compressor until a safe temperature is sensed.

Krueger in U.S. Pat. No. 4,409,795 discloses a demand defrost system. This invention is limited in that a photocell is required to sense the build-up of frost in a heat exchanger.

Tershak et al. in U.S. Pat. Nos. 4,481,785 and 4,528,821 disclose an adaptive defrost control system for a refrigerator. This invention is limited in that it controls the length of the interval between defrost operations in accordance with the number and duration of compartment door openings, the duration of a previous defrost operation as corrected by the temperature of the evaporator prior to defrost and the length of time the compressor has been energized.

Janke et al. in U.S. Pat. No. 4,530,218 disclose a refrigeration apparatus defrost control. This invention is limited in that it requires the use of a conventional frost sensor which may be an optical sensor, a pressure sensor or an acoustical sensor.

Bruchmuller in U.S. Pat, No. 4,532,806 discloses a sensor for monitoring the deposition of frozen fog and/or ice on a surface. This invention is limited in that it includes a vibration transmitting membrane and a vibration receiving membrane. When frost is deposited on the membranes, a damping effect takes place.

Sabin et al. in U.S. Pat. No. 4,608,832 disclose means and techniques useful for detecting frost on a fin of an evaporator. This invention is limited in that it is configured to measure the temperature gradient from one point on the fin to another point on the fin using a heat flux sensor. The technique is unreliable because it requires knowing where and how to locate the sensor on the fin, which varies from one installation to the next. While the temperature gradient on a fin is a function of frost buildup, the function is different for each installation. A critical limitation of this invention is that it does not provide structure that is capable of measuring the heat flux from the fin to the air. One embodiment of this invention includes the thermoelectric heat flow responsive device of U.S. Pat. No. 3,525,648, which device has the limitations described above.

Starck et al. in U.S. Pat. No. 4,671,072 disclose a sensor for detecting frost deposits. This invention is limited in that it relies on the use of a heat source and a heat sensor. When sufficient frost forms around the sensor, more heat is conducted from the heater to the sensor, which causes the temperature sensed by the sensor to increase.

White in U.S. Pat. No. 4,882,908 discloses a demand defrost control method and apparatus. This invention is limited in that it requires that a controller check outdoor and coil temperature to determine if a defrost cycle should be initiated.

Borton et al. in U.S. Pat. No. 4,993,233 disclose a demand defrost controller for refrigerated display cases. This invention is limited in that it requires temperature measurements taken at the outlet of the discharge air curtain and the inlet of the air return to determine the need for defrost.

Brace et al. in U.S. Pat. No. 5,051,645 disclose a frost sensor that incorporates an acoustic wave water phase change sensor. This device is limited in that an acoustic wave water phase change sensor is required.

Bahel et al. in U.S. Pat. No. 5,319,943 disclose a defrost control system for a heat pump. This invention is limited in that it requires measurement of the difference between the outdoor air temperature and the temperature of the outdoor coil.

Ridenour in U.S. Pat. No. 5,345,775 discloses a frost detection assembly for a refrigeration system. This invention is limited in that it requires the use of two thermistors, one touching the fin and one located about $1/16$ inch away. When the depth of ice accumulation on the fin reaches $1/16$ inch, the temperatures sensed by each of the thermistors become similar. A comparison of the temperatures is used to signal the initiation of a defrost cycle.

Szynal et al. in U.S. Pat. No. 5,493,867 disclose a fuzzy logic adaptive defrost control. This invention is limited in that it requires determination of the cumulative and continuous runs times of the compressor and defrost heater.

Nojiri in U.S. Pat. Nos. 5,522,232, 6,038,872 and 6,092,925 discloses a frost detection device. This invention is limited in that it requires the use of two temperature sensors, one of which has a cap and is a reference sensor and the other of which is in contact with air through small slits. When ice forms over the slits, the differential temperature between the two sensors approaches zero, and a defrost cycle is initiated. The invention also requires the cycling of the refrigerator's compressor to accentuate the temperature inertia differences.

Hollenbeck et al. in U.S. Pat. No. 5,692,385 disclose a system and method for initiating a defrost cycle. The invention is limited in that sensing of the speed or torque of the motor that drives the fan that moves air through the evaporator is required.

The background art is also characterized by non-patent publications. None of these publications teach the subject invention, but many of them reveal the need for more efficient defrost control.

Eckman, R. L. in "Heat Pump Defrost Controls: A Review of Past, Present and Future Technology" presented at the 1987 Winter Meeting of ASHRAE and published in the ASHRAE Transactions: Technical and Symposium Papers for that conference, (1987), pp. 1152–1156, describes the advantages and disadvantages of a variety of technologies for defrost control. The approach taken by the inventors of the subject invention is not mentioned.

Heinzen, R. A. in "How Adaptive Defrost Maintains Refrigeration System Efficiency" in Australian Refrigeration, Air Conditioning and Heating, (April 1988), pp. 12–16, 42–4, describes adaptive defrost control. The "K" variable as used in this reference represents a different variable from the "K" variable used herein.

Paone, N. et al. in "Fiber-optic ice sensors for refrigerators" in SPIE Fiber-Optic Sensors: Engineering and Applications, (March, 1991), pp. 129–130, 1511, describes a defrost control based on fiber-optic technology.

Energetics, Inc. in Refrigeration Systems Program Summary, DOE/CH/10093-120, (December, 1991), pp. 1–8, U.S. Department of Energy, Washington, D.C., describes the goals for the program, which include encouragement of the development of new energy-efficient refrigeration systems.

Borton, D. N. et al. in Development of a Demand Defrost Controller, (October, 1993), pp. i through 4–7, New York State Energy Research and Development Authority, Albany, N.Y., describes demand defrost control based on the temperature difference between the discharge and return of the display case air curtain in combination with several time settings.

Westphalen D. et al. in Energy Savings Potentialfor Commercial Refrigeration Equipment—Final Report, (June, 1996), pp. i through 3—3, U.S. Department of Energy, Office of Building Technologies, Washington, D.C., describes the energy-saving potential of a number of technologies, including demand defrost control.

The Office of Industrial Technologies, U.S. Department of Energy, in Energy Saving Intelligent Controller for Refrigeration (November, 2000), pp. 1–2, U.S. Department of Energy, Office of Industrial Technologies, Washington, D.C., describes the subject invention. This document was actually published at an unknown later date.

Stoecker, W. F. et al. in "Energy Considerations in Hot-Gas Defrosting of Industrial Refrigeration Coils," Report No. 2796, ASHRAE Project RP-193, in Energy Consideration in Hot-Gas Defrosting of Industrial Refrigeration Coils," presented at the 1983 Annual Meeting of ASHRAE and published in the ASHRAE Transactions: Technical and Symposium Papers for that conference, (1983), pp. 549–573, describes the use of hot-gas defrosting of industrial refrigeration coils.

There are a number of secondary parameters that can be measured to determine when a coil is frosted, as evidenced by the teachings of the patents and publications that describe the demand defrost technologies cited above. None of these devices measure the primary parameter of interest for a refrigeration system: the rate of heat transfer from the air to the refrigerant.

In summary, although a need is recognized for a demand defrost controller as evidenced by previous efforts, no suitable equipment is available. In particular, the background art does not teach the concept of incorporating a heat flux sensor into a frost sensor for measurement of the rate of heat transfer from the air to the refrigerant.

BRIEF SUMMARY OF THE INVENTION

A purpose of the invention is to provide a signal which can be use to initiate and terminate defrost cycles in industrial and commercial refrigeration systems in such a way as to reduce the overall energy consumed by the complete refrigeration system. Another purpose of the invention is to optimize the operation of evaporative heat exchangers and refrigeration systems.

A preferred embodiment of the invention is a frost sensor that can directly measure the total thermal resistance to heat flow from the air to the evaporative cooler fins. The frost sensor measures the reduction in heat flow due to the added thermal resistance of the ice (reduced conduction) as well as the reduction in heat flow due to the blockage of airflow (reduced convection) from excessive ice formation. This frost sensor triggers a defrost cycle when needed, instead of on a timed interval. Temperature sensors are incorporated into the frost sensor and are monitored to determine when to terminate the defrost cycle. This decreases the number of defrost cycles and the length of each defrost cycle to which a refrigeration system is subjected. A reduction in the total time a refrigeration system is defrosting increases the overall efficiency of the refrigeration process and thereby saves energy.

This disclosed demand defrost system also increases the cooling capacity of the refrigeration system by maximizing the cooling time compared to the defrost time. As a result, the refrigerated product is subject to fewer and shorter temperature excursions, thereby maintaining a higher level of product quality and reducing health risks for food products. Another advantage of a preferred embodiment of the invention is that it can be configured to trigger an alarm for any failure in the refrigeration system that limits the system's ability to cool product. The alarm threshold can be set to trigger prior to the warming of the refrigerated space so that no product is lost. Because this frost sensor measures heat flux, any sudden decline in heat flux indicates that the refrigeration system has failed. These failure modes include air blockage, fan failure, loss of refrigerant, compressor failure, etc.

Another advantage of the invention is that it can be used to monitor the build-up of dirt on the evaporative coil over time. A preferred embodiment of the invention can maintain a record of the heat flux immediately after defrost, and compare the measurement after the most recent defrost cycle to identify the slow loss of efficiency due to the build-up of dirt. A preferred embodiment of the invention can then provide an alarm that alerts the user to an efficiency decline of the cooling coil.

One object of the invention is to increase the efficiency of refrigeration systems. Another object to allow a defrost cycle to be initiated when needed, instead of on a fixed time interval. Yet another object of the invention is to allow termination of a defrost cycle when frosting has been reduced adequately. A further object of the invention is to reduce the number of defrost cycles and the length of each cycle. Another object of the invention is to conserve energy. Yet another object of the invention is to increase the cooling capacity of refrigeration systems. A further object of the invention is to allow a higher level of refrigerated product quality to be maintained. Another object of the invention is to trigger an alarm when either equipment failure or more permanent insulating accumulations than frost (e.g., dirt buildups) occur. Yet another object of the invention is to measure insulating accumulations with a heat flux sensor that accumulates the deposits at about the same rate as adjacent fins.

The invention is an apparatus and method for controlling the operation of a refrigeration system that comprises an evaporative heat exchanger that transfers heat from air being cooled to a refrigerant. The disclosed invention measures the heat flux or total thermal conductivity of the thermal path from the air to the refrigerant, recognizes the reduction in heat flux or total thermal conductivity due to the thermal insulation effect of the frost and due to the loss of airflow from excessive ice formation, and controls the defrosting of the system accordingly.

In a preferred embodiment, the invention includes a heat flux sensor that presents a side to the airflow that has a temperature that is within a few degrees of the temperature of the adjacent portion of the fin upon which the heat flux sensor is installed, which fin is being used to transfer heat from the airflow to the refrigerant.

A preferred embodiment of the invention is a frost sensor for mounting on an evaporative heat exchanger that is exposed to an airflow, the frost sensor comprising: a printed circuit board comprising an electrical circuit; a first temperature sensor that is mounted on the printed circuit board and that is electrically connected to the electrical circuit; a copper clip that is preferably fabricated from full-hard spring copper; a heat flux sensor that is mounted on said copper clip and that is electrically connected to the electrical circuit; a spring clip that is operative to hold the heat flux sensor or said copper clip and the first temperature sensor against a first cooling fin of the evaporative heat exchanger, and to hold a part of the printed circuit board against the first cooling fin on the side of the cooling fin opposite the side against which the heat flux sensor or copper clip is being held; a second temperature sensor that is mounted on the printed circuit board in such a manner that the airflow impinges on the second temperature sensor before it impinges on the first cooling fin; and an electrical connector that is mounted on the printed circuit board and electrically connected to the electrical circuit. In a preferred embodiment, the disclosed frost sensor's heat flux sensor is mounted on the copper clip by means of an adhesive (e.g., a thin layer of epoxy) and the copper clip is held against the first cooling fin.

In another preferred embodiment, the disclosed frost sensor further comprises a third temperature sensor that is in thermal contact with the evaporative coil at a location where ice tends to melt the slowest and that is thermally insulated from said airflow.

Another preferred embodiment of the invention is a defrost control system that comprises the disclosed frost sensor. The defrost control system comprises a signal processor (e.g., a microcontroller) and has the capability of controlling the temperature in the refrigerated zone, eliminating the need to interface with various commercially-available thermostatic controls. The defrost control system includes the disclosed defrost sensor and convention control components, which conventional components are known in the art and disclosed in the patents incorporated by reference herein above.

Another preferred embodiment of the invention is a refrigeration system that comprises the disclosed frost sensor. In refrigeration systems using advance control systems, the disclosed frost sensor can be used in combination with a processor that operates in accordance with the defrost algorithm disclosed herein. The refrigeration system includes the disclosed defrost sensor and conventional refrigeration components, which conventional components are known in the art and disclosed in the patents incorporated by reference herein above.

In another preferred embodiment, the invention is a device for sensing frost on a cooling fin of an evaporative heat exchanger that is subjected to an airflow, the device comprising: a heat flux sensor that is in thermal contact with and located on one side of the fin; a thermal insulator (e.g., a portion of a printed circuit board) that is in thermal contact with the fin and located on the other side of the fin, opposite the location of the heat flux sensor; a first temperature sensor that is in contact with the airflow before the airflow is in contact with the fin; and a second temperature sensor that is in thermal contact with the fin and that is thermally insulated from the airflow.

In yet another preferred embodiment of the invention, the disclosed device further comprises a third temperature sensor that is in thermal contact with the evaporative heat exchanger at a location where ice tends to melt the slowest and that is thermally insulated from the airflow. In a preferred embodiment, the device's heat flux sensor is a differential thermopile and the thermal insulator is at least a portion of a printed circuit board.

A further preferred embodiment of the invention is a sensor for characterizing the heat-transfer effectiveness of an evaporative coil that comprises a plurality of cooling fins that are subject to insulating accumulations, the sensor comprising: means (e.g., a heat flux sensor) for measuring the heat flow from an airflow to a first cooling fin that produces a first signal; means (e.g., a first temperature sensor) for measuring the temperature of the first cooling fin that produces a second signal; and means (e.g., a second temperature sensor) for measuring the temperature of the airflow that produces a third signal; wherein the three signals are used to quantify the total thermal conductivity of the accumulations. In a preferred embodiment, the third signal is used to determine when the coil has been adequately defrosted during a defrost cycle. In another preferred embodiment, the sensor also comprises means (e.g., a computer) for scheduling the defrost cycle for the evaporative coil.

In another preferred embodiment, the disclosed sensor further comprises means (e.g., a third temperature sensor) for measuring the temperature of a second cooling fin that produces a fourth signal, the second cooling fin being located where ice tends to melt more slowly than it does on the first cooling fin during a defrost cycle. Preferably, the means for measuring the temperature of a second cooling fin is installed in a region of the evaporative coil where ice (frost) tends to melt the slowest. In a preferred embodiment, the fourth signal is used to determine when the coil has been adequately defrosted during a defrost cycle.

Another preferred embodiment of the invention is a device for sensing frost on a cooling fin of an evaporative heat exchanger, the device comprising a heat flux sensor that is in thermal contact with the fin. The heat flux sensor produces signals that are used to control the defrosting of the evaporative heat exchanger.

The invention is also a method of using or operating the disclosed apparatus. In a preferred embodiment, the invention is a method for defrosting a refrigeration system that includes an evaporative heat exchanger having a fin that is exposed to an airflow and that is subject to an insulating accumulation, the method comprising: measuring the heat flux from the airflow into the fin, the temperature of the fin and the temperature of the airflow; calculating the total thermal conductivity or total thermal resistance value of the insulating accumulation (should an accumulation exist); and initiating a defrost cycle when the total thermal conductivity or total thermal resistance value reaches a predetermined setpoint. Preferably, the disclosed method further comprises terminating said defrost cycle when the temperature of the fin reaches a target temperature.

In a preferred embodiment, the disclosed method also comprises comparing heat flux data collected at a previous time with heat flux data collected at a subsequent time; and initiating an alarm procedure if the comparison indicates that the measured heat flux is trending downward.

Yet another embodiment of the invention is a technique for operating a refrigeration system that includes an evaporative heat exchanger having a fin that is exposed to an airflow and that is subject to an insulating accumulation, the technique comprising: measuring the heat flux from the airflow into the fin, the temperature of the fin and the temperature of the airflow; determining whether the heat flux is below an expected value; if the heat flux is not below the expected value, calculating the total thermal conductivity or total thermal resistance value of the insulating accumulation and applying a setpoint adjustment factor; resetting the system timers; determining whether the system is in an auto defrost mode; if the system is in an auto defrost mode, determining whether the heat flux or the total thermal conductivity or total thermal resistance value has reached a setpoint; if the system is not in an auto defrost mode, determining whether the time until defrost has expired; and if either the heat flux or the total thermal conductivity or total thermal resistance value has reached a setpoint or the time until defrost has expired, initiating a defrost cycle.

In another embodiment, the disclosed technique further comprises: if the heat flux is below the expected value, determining if the heat flux is downward trending; if the heat flux is downward trending, concluding that an evaporator dirt accumulation is indicated, sending an evaporator dirt accumulation alarm message and setting the system to a timer mode; and if the heat flux is not downward trending, concluding that an equipment failure is indicated, sending an equipment failure alarm message and setting the system to a time mode.

A further preferred embodiment of the technique further comprises: if a defrost cycle has been initiated and the system is in an auto defrost mode, determining whether the fin temperature has reached a fin temperature target; if the fin temperature has reached the fin temperature target, comparing the actual defrost time to the target defrost time; if the actual defrost time is less than the target defrost time, decreasing the setpoint adjust factor; if the actual defrost time is greater than the target defrost time, increasing the setpoint adjust factor; and if the system is not in the auto defrost mode, determining whether the time until defrost has expired.

Yet another preferred embodiment of the invention is a process for control of frost in a system that transfers heat from air to a refrigerant along a thermal path, the process comprising: measuring the thermal conductivity of the thermal path from the air to the refrigerant; recognizing a reduction in thermal conductivity due to the thermal insulation effect of the frost and due to the loss of airflow from excessive ice formation; and controlling the defrosting of the system.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings that illustrate presently preferred embodiments of the invention. In the drawings:

FIG. 6 is an exploded view of a preferred embodiment of the invention.

FIG. 7 is a perspective view of the side of a preferred embodiment of the invention showing the side of the printed circuit board that faces away from the fin.

FIG. 8 is a perspective view of the side of a preferred embodiment of the invention showing the side of the printed circuit board that faces the fin.

Figure 1:
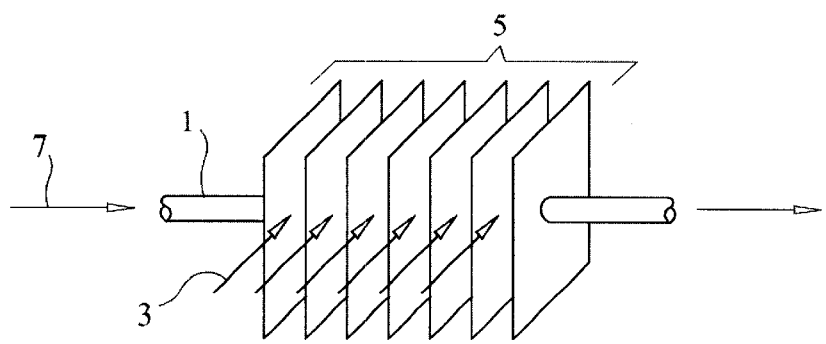
FIG. 1 is schematic diagram illustrating the environment of a preferred embodiment of the invention. Only a limited number of cooling fins are shown for clarity.

The following reference numerals are used to indicate the parts and environment of the invention on the drawings:

evaporative cooling coil, evaporative heat exchanger
3 airflow, air
5 cooling fins, fins
7 refrigerant
11 frost sensor
13 heat flux sensor
15 first temperature sensor
17 second temperature sensor
19 copper clip
21 printed circuit board, PCB
23 mechanical fastener, spring clip
25 electrical connector
27 controller, computer, processor
29 cooling fin, fin
31 frost, ice
101 heat flux averaging step
103 heat flux comparison step
105 calculation step
107 resetting step
109 first mode determination step
111 setpoint comparison step
113 time comparison step
115 defrost step
121 trend comparison step
123 dirt accumulation step
125 equipment failure step
127 alarm step
131 alarm message step
133 set timer mode step
135 go-to-start step
139 second mode determination step
141 fin temperature comparison step
143 defrost time comparison step
145 decrease adjust factor step
147 increase adjust factor step
149 defrost time comparison step

DETAILED DESCRIPTION OF THE INVENTION

Referring to FIG. 1, the environment of a preferred embodiment of the invention is illustrated. Evaporative cooling coil or evaporative heat exchanger 1 of a refrigeration system accumulates frost when warmer moist airflow 3 is blown across cooling fins 5 which are at a temperature below freezing. This frost will continue to build until coil 1 is completely encapsulated in ice, blocking the air passages, or until coil 1 is defrosted. The ice is one example of an insulating accumulation that can affect the performance of the system. Dirt is another example.

In the background art, the defrost cycle is typically controlled by time clocks. These time clocks are set to defrost more often and for longer periods of time than necessary to insure that even under the most extreme environmental conditions evaporative coil 1 does not completely freeze and that the accumulated frost is completely removed during the defrost mode. Frost on fins 5 reduces the heat transfer between air 3 and refrigerant 7 in two ways. First, the frost acts as a thermal insulator on the fins thereby reducing heat conduction to refrigerant 7. Second, when sufficient frost has formed, the air passages between fins 5 become blocked with ice thereby reducing air contact with the cooled surfaces of the coil fins (reduced convection).

Figure 2:
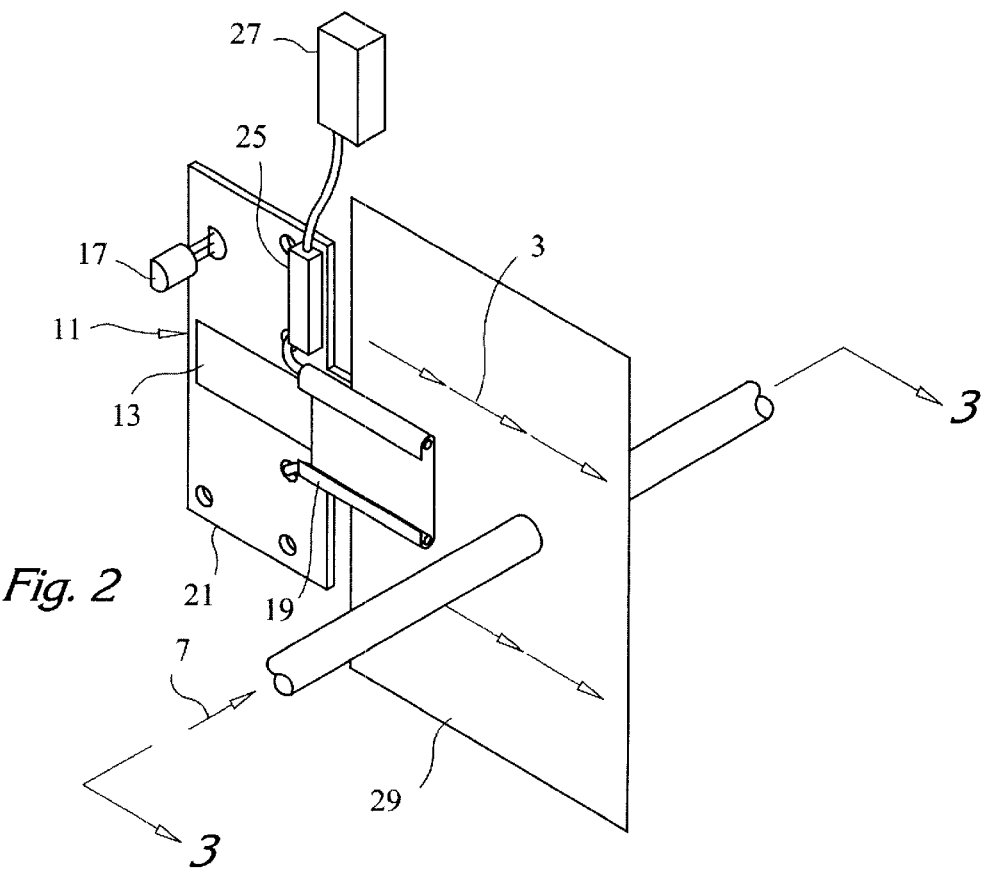
FIG. 2 is a schematic diagram illustrating the installation of a first preferred embodiment of the invention.

Referring to FIG. 2, a first preferred embodiment of frost sensor 11 is illustrated installed on fin 29. This embodiment of frost sensor I 1 incorporates heat flux sensor 13, first temperature sensor 15 (not shown) and second temperature sensor 17. Heat flux sensor 13 measures the heat flux from air 3 to fin 29 of an evaporative heat exchanger. Second temperature sensor 17 is located so that it can measure the temperature of the incoming air 3.

In a preferred embodiment, heat flux sensor 13 is fixed to copper clip 19 which is attached to printed circuit board 21 by means of mechanical fastener or clip 23. Printed circuit board 21 comprises an electrical circuit (not shown) to which heat flux sensor 13 and temperature sensors 15 and 17 are electrically connected. Electrical connector 25 connects the electrical circuit to controller 27. Frost sensor 11 is assembled on small printed circuit board (PCB) 21 which serves two functions. The first function of circuit board 21 is to insulate the side of fin 29 opposite the side against which heat flux sensor 13 is held. The second function of the PCB 21 is to provide a surface for mechanical and electrical connections.

Figure 3:
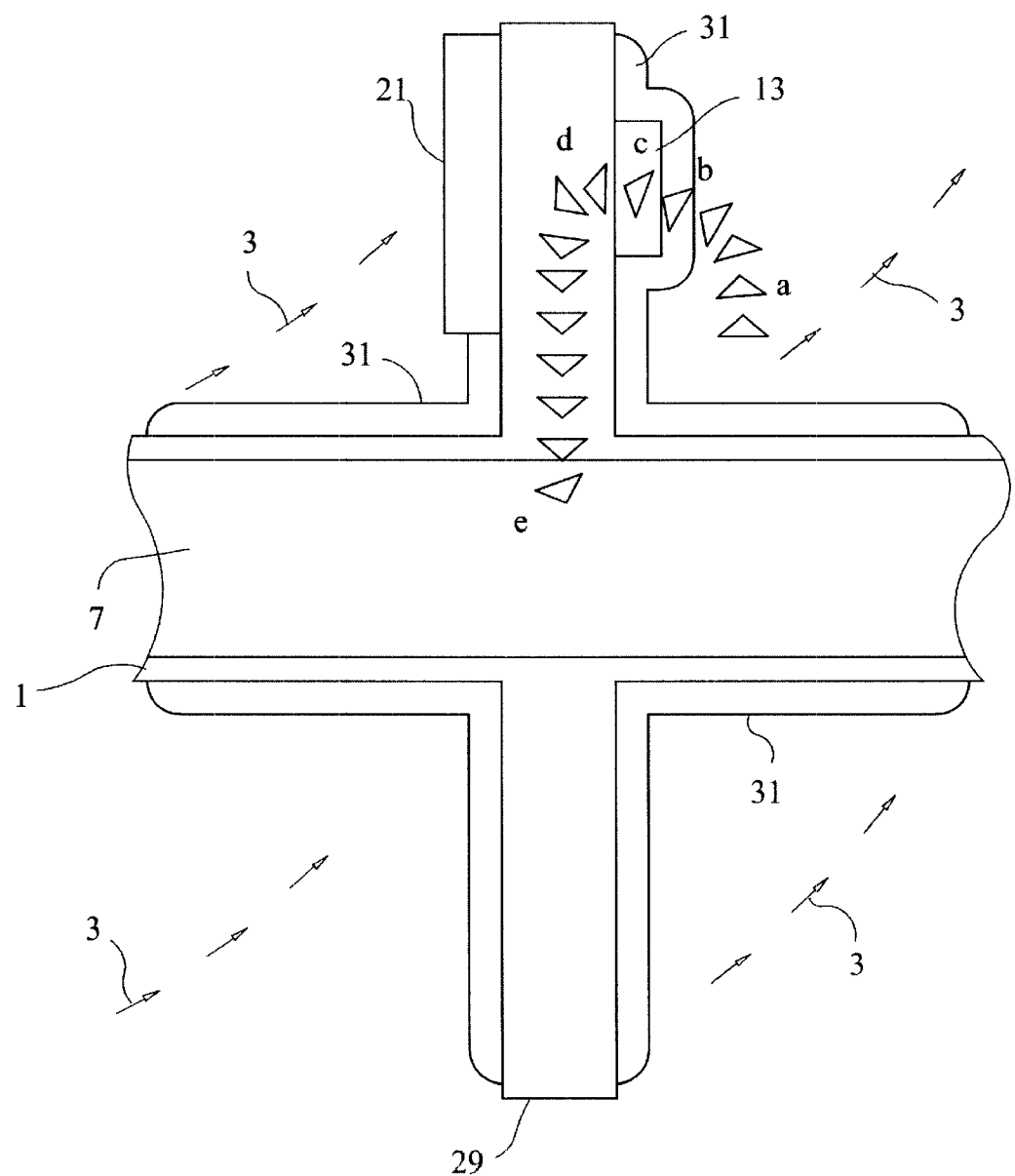
FIG. 3 is a schematic diagram illustrating the heat flow path associated with use of a preferred embodiment of the invention.

Referring to FIG. 3, in a schematic representation, a preferred embodiment of frost sensor 11 is shown clipped onto one fin 29 of the cooling fins 5 shown in FIG. 1. Because of the insulation provided by the material of PCB 21, the heat flow path is as follows: (a) from passing air 3 to the surface of ice 31, (b) through ice 31, (c) through heat flux sensor 13, (d) through cooling coil fin 29, (e) from cooling coil 1 to refrigerant 7.

Referring again to FIG. 3, frost sensor 11 makes measurements of the heat flux (Q), the temperature of airflow 3 (Tair) and the temperature of fin 29 (Tfin). The thermal conductivity of the conduction path from the air-exposed side of the heat flux sensor to the refrigerant ("c" through "e") remains constant throughout the frost/defrost cycle. As frost or ice 31 forms, the thermal conductivity of the heat flux path from air 3 to heat flux sensor 13 ("a" through "b") is reduced due to the insulation effect of ice 31, which can be illustrated by examining the equation for heat conduction which follows:

$$Q=kA(T1-T2)/L$$

where

Q is the heat flow k is the thermal conductivity

A is the cross-sectional area of the heat transfer path

L is the length between T1 and T2

(T1–T2) is the temperature difference at two points

A preferred embodiment of frost sensor 21 measures Q directly as well as Tfin and Tair. For the purposes of this analysis, the terms "kA/L" can be combined, and referred to as K, where K is the total thenrnal conductivity. K can also be thought of as 1/R, where R is total thermal resistance, and, thus, K=Q/(T1–T2).

Frost sensor 21 measures K, which is an indicator of how efficiently heat is being transferred from air 3 to refrigerant 7. As frost 31 forms, K decreases and as airflow 3 is reduced due excessive to ice formation, K decreases to essentially zero. If Tair and Tfin remained constant under all conditions, then simply measuring Q would give a measurement proportional to K. However, the cooling fin temperature may vary as a function of the level of ice 31 on the fin 29 depending on the plumbing configuration. By measuring Q and dividing it by (Tair-Tfin), as called for by a preferred embodiment of the invention, frost sensor 21 can determine K in all plumbing configurations.

In an alternative embodiment, frost sensor 21 measures only Q and does not measure Tair or Tfin. In this embodiment, frost sensor 21 includes heat flux sensor 13 and does not include temperature sensors 15 and 17. Furthermore, only Q is used to characterize how efficiently heat is being transferred from air 3 to refrigerant 7.

Figure 4:
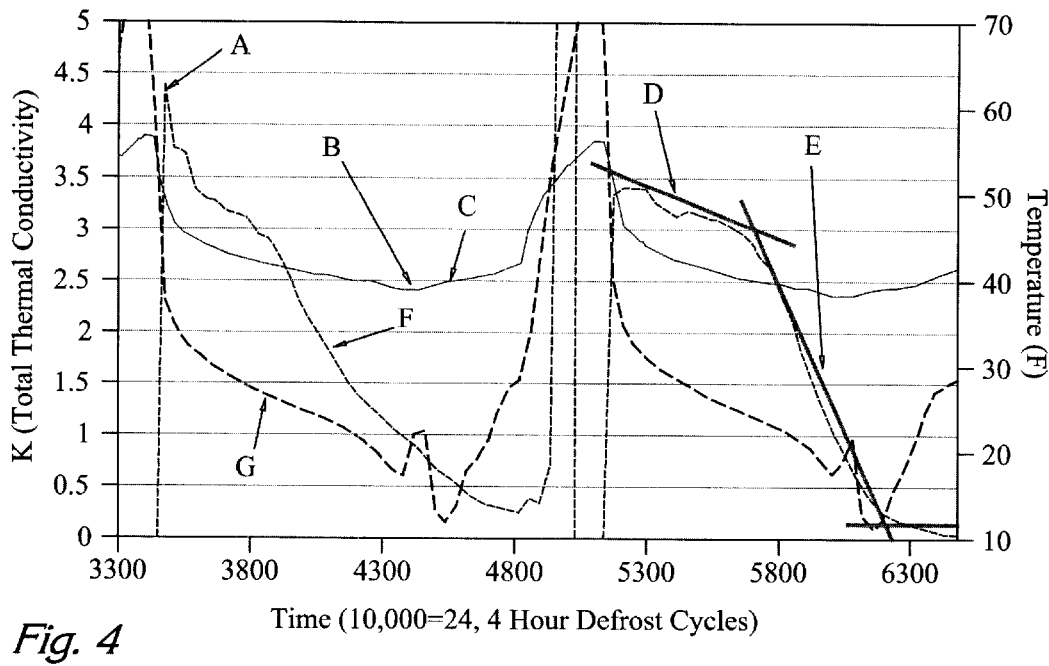
FIG. 4 is a graph of typical data from a preferred embodiment of a frost sensor incorporated into a walk-in cooler/freezer.

Referring to FIG. 4, typical data produced by a frost sensor 11 are presented. A preferred embodiment of frost sensor 11 provides two useful signals that are used to control the defrosting of evaporative coils. The first signal (represented by line F on FIG. 4) is K (read on the scale to the left) as described above, which is used to initiate the defrost cycle. The second signal (not shown) is the temperature of the fin, Tfin, which is used to terminate the defrost cycle once the coil has reached some pre-determined temperature during defrost, e.g., 50° or 60° F. This approach is called temperature termination and is a well known method of controlling the length of a defrost cycle. Also shown on FIG. 4 is the refrigerated room temperature, which is represented by line C and read on the scale on the right, and the air temperature leaving the heat exchanger, which is represented by line G and also read on the scale on the right.

Referring again to FIG. 4, the previous defrost cycle ends at point A on line F. At point B on line C, the room temperature begins to increase due to airflow blockage by ice. Trend line D tracking a first portion of line F shows that heat flux is decreasing due to reduced conduction caused by ice formation. Trend line E tracking a second portion of line F shows that heat flux is dropping rapidly due to reduced convection caused by ice formation which is blocking the airflow.

In operation, the operator uses the time required to defrost the coil to calibrate frost sensor 11 as installed. It is necessary to learn the optimum point to initiate defrost. because the characteristics of a given installation of frost sensor 11 may vary significantly. Some of the ways frost sensor 11 installation may vary include the following:

(A) frost sensor 11 located in a particularly warm or cold part of evaporative coil 1, (B) uneven airflow pattern through evaporative coil 1, (C) level of thermal contact between frost sensor 11 and fin 29, (D) frost sensor 11 located in a rapidly frosting region of exchanger 1 or located in a slowly frosting region of evaporative coil 1.

Upon initial installation of frost sensor 11, a calibration procedure is begun by initiating a defrost cycle based on the recommendation of the manufacturer of the evaporative coil or refrigeration system. The time required to defrost coil 1 is measured and related to the signals produced by frost sensor 11 based on measurements taken just prior to the initiation of the defrost cycle. If the required length of the defrost cycle is less than the time specified in the system manufacturer's design specification (generally 15 to 20 minutes), the next frosting period is lengthened by the operator. The length of the defrost cycle is then measured again and related to the signals produced by frost sensor 11 based on measurements taken just prior to the initiation of the defrost cycle. The frosting period is extended in this fashion until the length of the defrost cycle is within the manufacturer's design specification. From this point forward, frost sensor 11 is calibrated and can be used to initiate defrost cycles.

Figure 5:
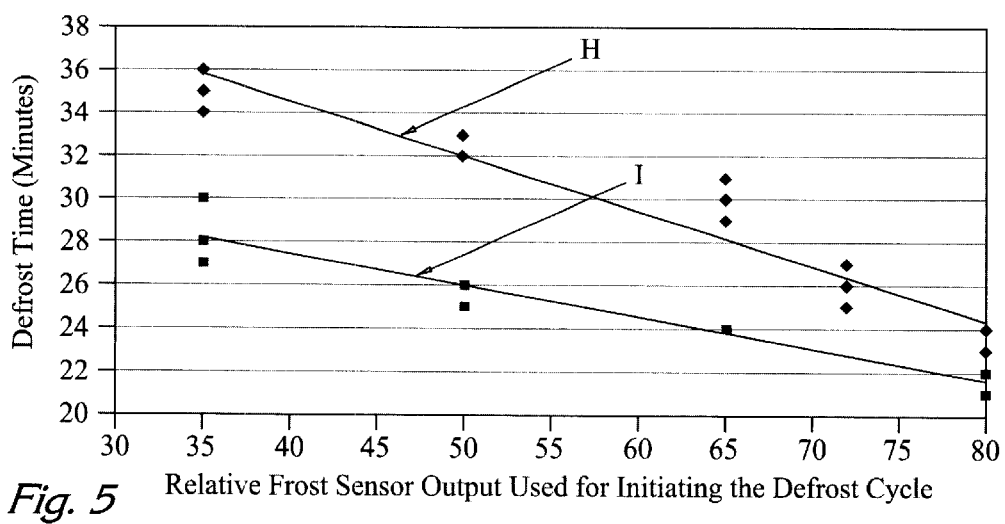
FIG. 5 is a graph of typical data used in calibration of a preferred embodiment of the invention.

An example of how calibration data are analyzed is presented in FIG. 5. At the end of each defrost cycle, the time to defrost is measured. The time to defrost is the time it takes to reach the pre-determined setpoint for fin temperature (e.g., 50 to 60 degrees F.). Thus, for each frost-defrost cycle, one data point is produced that relates the output of frost sensor 11 (heat flux or K) to the length of time it takes to defrost the coil at that frost sensor output signal level. FIG. 6 shows a mapping for two very different installation techniques. One installation technique, represented by line H, involves bending the neighboring fin away from fin 29 upon which frost sensor 13 is installed to allow maximum airflow. This means that even when the air gap adjacent to neighboring fins is sealed by insulating accumulations, airflow 3 can still pass by frost sensor 11. An alternative installation technique, represented by line I, is to locate the neighboring fin (by bending it) very close to frost sensor 11. With this approach, the air gap adjacent to frost sensor 11 is sealed by frost earlier than the air gaps adjacent to neighboring fins. These two lines, line H and line I, represent the extremes of installation technique. As is apparent from the relationships shown in FIG. 5, the defrost time is directly related to the frost sensor signal, K. In fact, if one mapped the frosting time to either K or the defrosting time, no recognizable trend would be apparent. This reveals the need for the heat flux measurement.

If nothing in the environment of the system ever changed rapidly, it would be possible to use the length of the defrost cycle to initiate subsequent defrost cycles without reliance on frost sensor 11. However, unusual circumstances or changes in environmental conditions can occur which can significantly change the length of the desirable frosting period. Such changes could be due to weather fronts, HVAC problems, the differences between ambient conditions during day and night or the freezer being filled or emptied. By making direct measurements of the total thermal conductivity of insulating accumulations on coil 1, a defrost cycle is always initiated at an appropriate level of frosting even when environmental changes occur rapidly.

Frost sensor 11 may also be used to determine the level of dirt that has accumulated on evaporative coil 1. By monitoring the initial heat flux immediately after the completion of a plurality of defrost cycles, it is possible to measure the level of dirt accumulation on the sensor (which is similar to the level of dirt accumulation on fins 5). The initial heat flux measured immediately after a defrost cycle will decrease over subsequent freeze-thaw cycles because the increasing dirt accumulation will act as an insulator (as ice 31 does). Immediately after a defrost cycle has occurred, no frost is present so that any reduction in K is due to dirt accumulation. In addition, the time for defrost can be monitored over time to determine the level of dirt accumulation. The time required for defrosting to be completed also provides a useful measure of the level of dirt accumulation on evaporative coil 1, because frost sensor 11 initiates the defrost cycle at the same K value over time (after the initial calibration period). Dirt (which has no latent heat of fusion) does not require a lengthy defrost cycle to warm to the 50° to 60° F. setpoint compared to ice 31 which has a large latent heat of fusion to overcome. Therefore, the shortening of the defrost cycle when cycles are initiated at the same K value is a direct indicator of the level of dirt accumulation.

An important advantage of frost sensor 11 is that it can be used to produce an alarm signal if any part of the refrigeration system fails to operate properly. This is possible because all failure modes of the refrigeration system lead to a reduction of heat flux at evaporative coil 1. For example, if the compressor fails, the solenoid valves fail or the evaporative coil fan fails, the heat flux will be dramatically reduced virtually immediately. This means that an alarm signal can be produced prior to the warming of the refrigerated space so that corrective action can be taken prior to the loss of product.

Another preferred embodiment of frost sensor 11 comprises four sensors. One sensor is heat flux sensor 13. A variety of heat flux sensors appropriate for incorporation into the invention are commercially available from several manufacturers, including Captec of Villeneuve D'Asco (Lille), France or Pennington, N.J. and RdF Corporation of Hudson, N.H.

A preferred heat flux sensor is manufactured by RdF Corp. of Hudson, N.H. The preferred heat flux sensor is RdF Model 27160, which is a differential thermopile. With this design, heat passing through a calibrated polyimide membrane produces a small temperature differential. The signal is proportional to the difference in temperature and the number of junctions in the thermopiles. The sensor is a thin film of kapton and comprises a series of thermocouples wired together to form a thermopile. While the indicated heat flux sensor is preferred, many other heat flux sensors could be used. An important criterion for the selection of a heat flux sensor for incorporation into the invention is that it have a relatively low thermal resistance or thermal impedance. The preferred RdF heat flux sensor has a thermal impedance of $0.01°$ F./BTU/(ft$^2$·hr). The preferred shape for the heat flux sensor is flat and thin.

In a preferred embodiment, heat flux sensor 13 presents a side to airflow 3 that, in use, has a temperature that is within about three degrees F of the temperature of the adjacent portion of fin 29 upon which heat flux sensor 13 is installed. In this embodiment, the difference between the temperature of the side of heat flux sensor 13 exposed to airflow 3 (for example, by its being in thermal contact with copper clip 19 which is exposed to airflow 3) and the temperature of a portion of 13 fin adjacent to heat flux sensor 13 is a result-effective variable that has been optimized by the applicants. In another preferred embodiment, heat flux sensor 13 is configured to measure the heat flow from airflow 3 to fin 29.

The other three sensors incorporated into this preferred embodiment of the invention are temperature sensors. Preferably, two of the three sensors to be used are Model TMP36GT9 temperature sensors in a TO-92 package, manufactured by Analog Devices of Norwood, Mass. The third sensor is an Analog Devices Model TMP36GS temperature sensor in an SO-8 package. While the indicated temperature sensors are preferred, many types of temperature sensors could be used. Important selection criteria for the temperature sensors are (1) the sensor's mechanical packaging allows measurement of the temperature at the desired points and (2) the sensor does not significantly affect airflow.

In this preferred embodiment, printed circuit board 21 is used to make all the electrical connections and to act as a thermal insulator on the opposite side of fin 29 from heat flux sensor 13. Printed circuit board 21 also provides a convenient mechanical mounting means for the sensor elements. In alternative embodiments, a conventional insulating means (e.g., a block of plastic or rubber foam) is used to provide the thermal insulation function.

Preferably, heat flux sensor 13 is attached to copper clip 19 made of full-hard spring copper using a thin layer of epoxy (not shown). Heat flux sensor 13 can be placed on either side of copper clip 19 (either pressing against fin 29 or being exposed to airflow 3). Preferably, heat flux sensor 13 is mounted on the side of copper clip 19 that faces fin 29 because frost does not appear to form on plastic quite the same way that it forms on metal. Because the invention acts as a frost sensor, it is desired that frost form on frost sensor 11 as similarly as possible to how it forms on evaporative coil fins 5. Copper is preferred for copper clip 19 because it is highly thermally conductive, but aluminum or any other highly thermally conductive material may be used.

Spring copper is used for spring clip 23 because it is designed to press heat flux sensor 13 against fin 29 to obtain good thermal contact. Using normal copper for fabrication of spring clip 23 is not preferred as it would simply bend and not provide the spring force necessary.

Heat flux sensor 13 can be directly glued to fin 29, but this approach is time consuming. For this reason, the preferred method for attaching heat flux sensor 13 to fin 29 is to use mechanical spring clip 23 so that frost sensor 11 can be easily installed and moved to another location on evaporative coil 1. Performance of frost sensor 13 can be slightly improved if during installation, a small dab of thermal cream (not shown) is placed on fin 29 where heat flux sensor 13 will be located.

In this preferred embodiment, one of the two TO-92 type temperature sensors is mounted on PCB 21 in such a way that airflow 3 moves first across temperature sensor 17 and then across heat flux sensor 13. Temperature sensor 17 is referred to as the air temperature sensor and the signal it produces is used in calculating the thermal conductivity (or the thickness) of ice 31. The SO-8 type temperature sensor 15 is mounted on PCB 21 directly under heat flux sensor 13. Preferably, temperature sensor 15 is mounted upside down so that so that the top of the temperature sensor is flush with the bottom of heat flux sensor 13 and the leads of temperature sensor 15 are located on the far side of PCB 21 compared to the heat flux sensor. The circuit on PCB 21 is on the side not touching fin 29. A square hole is cut in PCB 21 the same shape as the integrated circuit chip that comprises temperature sensor 15. The hole is not so large as to let the metal leads of the clip go through the hole. The surface mount chip is mounted upside down on the side of PCB 21 opposite the side that is against fin 29, so that the leads of the chip connect to the circuit which is on the side of PCB 21 not touching fin 29, but the body of the chip is the square hole cut in PCB 21. This configuration causes heat flux sensor 13 to press against one side of fin 29 and temperature sensor 15 to press against the opposite side of fin 29. Temperature sensor 15 provides a signal that characterizes the temperature of fin 29 for use in the calculation of the thermal conductivity (or the thickness) of ice 31.

In this preferred embodiment, the third temperature sensor (not shown) is either a TO-92 or a SO-8 style temperature sensor. It is located at a distance from PCB 21. The third temperature sensor is located by the installation technician in a region of evaporative coil 1 where the ice tends to melt the slowest. This is generally in an area of poor airflow and towards the top of evaporative coil 1. A preferred mounting means is to use an assembly identical to the frost sensor module with only the fin temperature sensor populated on the PCB. The signal produced by this third temperature sensor is used to terminate the defrost cycle. When this temperature sensor reaches a predetermined temperature (e.g., 50° F.), the coil is assumed to be frost-free.

FIG. 6 shows an exploded view of all the components of this preferred embodiment of frost sensor 11. Spring clip 23 is fitted through the two holes in the middle of PCB 21 and the long straight arms of spring clip 23 fit into channels in copper clip 19. Spring clip 23 is designed to put a mechanical pressure downward (toward PCB 21) on copper clip 19 (under which is located heat flux sensor 13).

Referring to FIG. 7, a perspective view of a preferred embodiment of frost sensor 11 is presented. The side of PCB 21 that faces away from fin 29 (not shown) is in view. First temperature sensor 15 is located in a hole in PCB 21 so it can measure the temperature of fin 29 (not shown).

Referring to FIG. 8, another perspective view of a preferred embodiment of frost sensor 11 is presented. The side of PCB 21 that faces toward fin 29 (not shown) is in view. Temperature sensor 15 and a portion of heat flux sensor are illustrated with dashed lines to indicate that they are located beneath copper clip 19 in FIG. 8.

Figure 9:
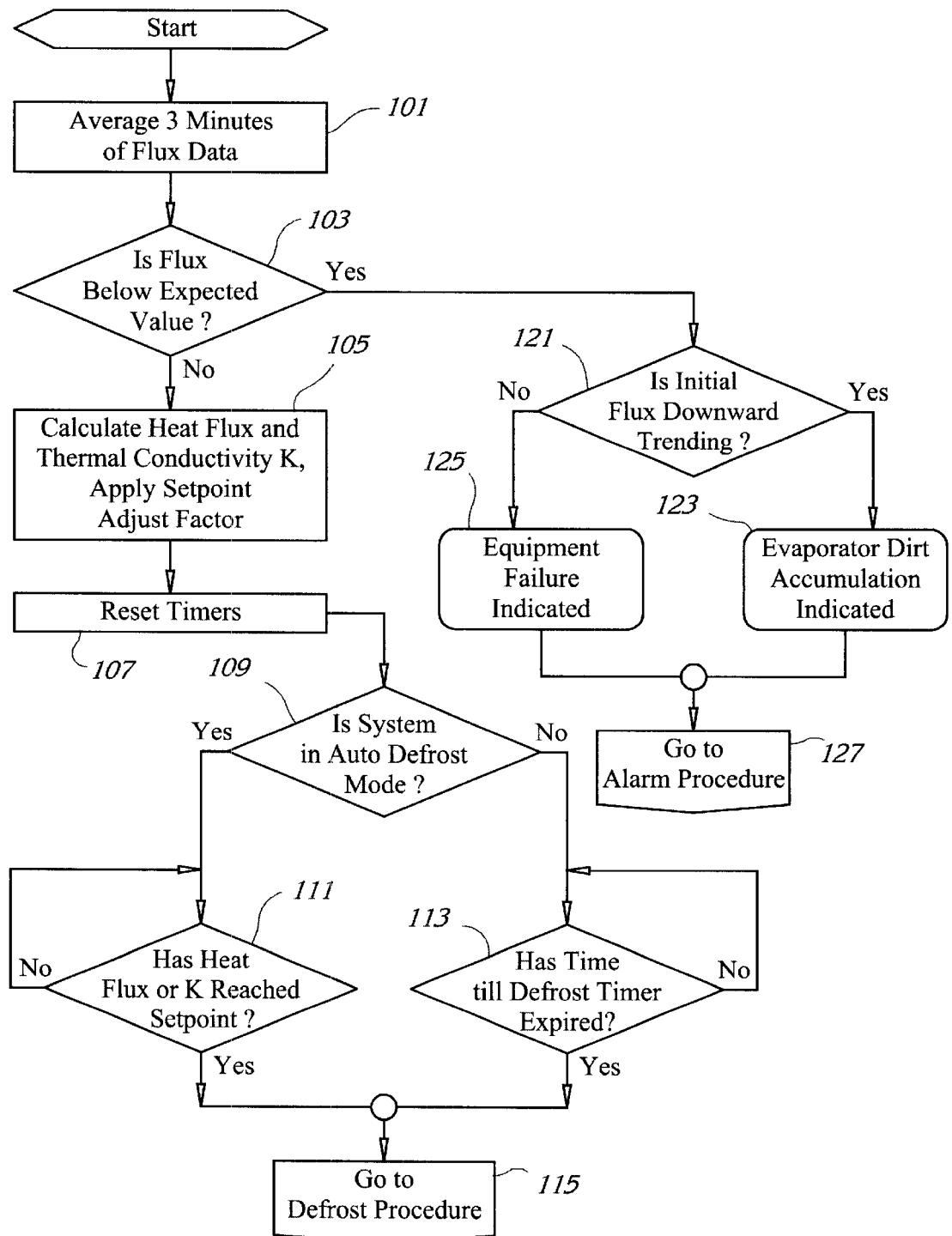
FIG. 9 is a schematic block diagram illustrating the steps involved in a preferred embodiment of the invention.

Referring to FIG. 9, a schematic block diagram of the software program is presented that operates controller or computer 27 in a preferred embodiment of the invention. The software program executes a technique for operating a refrigeration system that includes an evaporative heat exchanger having a fin that is exposed to an airflow and that is subject to an insulating accumulation. Heat flux averaging step 101 involves averaging about three minutes of heat flux data obtained by measuring the heat flux from the airflow into the fin, the temperature of the fin and the temperature of the airflow. Heat flux comparison step 103 involves determining whether the heat flux is below the expected value established during the calibration procedure described earlier. If the heat flux is not below the expected value, calculation step 105 is executed which involves calculating the total thermal conductivity or total thermal resistance value of the insulating accumulation and applying a setpoint adjustment factor.

Even after the initial calibration phase, the time to complete a defrost cycle is monitored. If the time for defrost to occur drifts out of the acceptable range (e.g., user setpoint +/–about 3 minutes) then the setpoint is slightly modified. For example, an initial calibration determines that, at a setpoint of 50 percent of the initial flux (or K value), the defrost cycle takes 20 minutes and 20 minutes is the desired defrost period as entered by the operator. If, as time passes, it is determined that when a defrost is triggered at 50 percent it is now taking 24 minutes instead of the desired 20 minutes, then the setpoint is adjusted up to 55 percent for the next cycle. Adjustments continue until the actual defrost period is within a few minutes of the desired defrost period. The time constant for these changes is very long and, thus, the setpoint is not modified significantly between consecutive defrost cycles. Thus, step 105 compensates for minor fluctuations in dirt level and other operating parameters.

Resetting step 107 involves resetting the system timers. In a preferred embodiment of the invention there are three system timers. The 'time till next defrost' timer and the 'defrost length' timer are both countdown timers and are used only in timer mode. They are reset to initial values as determined by user input and will then countdown to zero. The 'actual defrost time' timer will be reset to zero and count up to represent the duration of the defrost while in auto mode. First mode determination step 109 involves determining whether the system is in an auto defrost mode. In the timer mode, the system relies only on a time clock and a thermostat; there is no demand defrost function. In the auto mode, the system is relies on demand defrost. In both modes, the thermostat function occurs. A timer mode is needed in case an alarm condition occurs. An alarm is indication that something is not working and the output from the sensors cannot be trusted. When the alarm is turned on, the system is switched to the timer mode and waits for the operator to arrive.

If the system is in an auto defrost mode, setpoint comparison step 111 is executed which involves determining whether the heat flux or the or the total thermal conductivity or total thermal resistance value has reached a setpoint. If the system is not in an auto defrost mode, time comparison step 113 is executed which involves determining whether the time until defrost has expired. If either the heat flux or the total thermal conductivity or total thermal resistance value has reached a setpoint or the time until defrost has expired, defrost step 115 is executed which involves initiating a defrost cycle.

Figure 10:
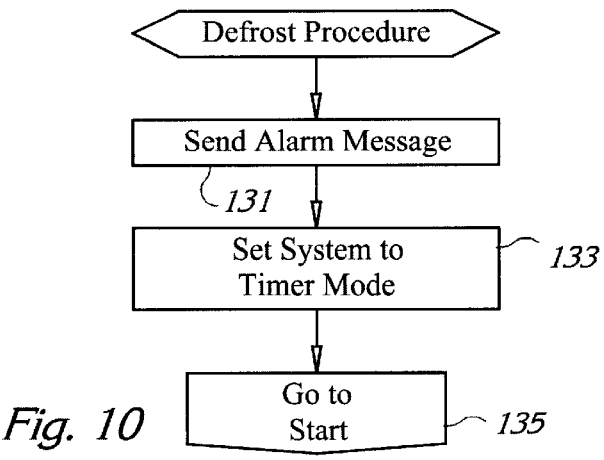
FIG. 10 is a schematic block diagram illustrating the additional steps involved in a preferred embodiment of the invention.

If flux comparison step 103 indicates that the heat flux is below the expected value, trend comparison step 121 is executed which involves determining if the heat flux is downward trending. If the heat flux is downward trending, dirt accumulation step 123 is executed which involves concluding that an evaporator dirt accumulation is indicated and alarm step 127 is executed which involves executing the alarm procedure. As is indicated on FIG. 10, the alarm procedure includes executing alarm message step 131 which, in this case, involves sending an evaporator dirt accumulation alarm message, executing set timer mode step 133 which involves setting the system to a timer mode and executing go to start step 135. If the heat flux is not downward trending, equipment failure step 125 is executed which involves concluding that an equipment failure is indicated. As is indicated on FIG. 10, the alarm procedure includes executing alarm message step 131 which, in this case, involves sending an equipment failure alarm message, executing set timer mode step 133 which involves setting the system to a time mode and executing go-to-start step 135.

Figure 11:
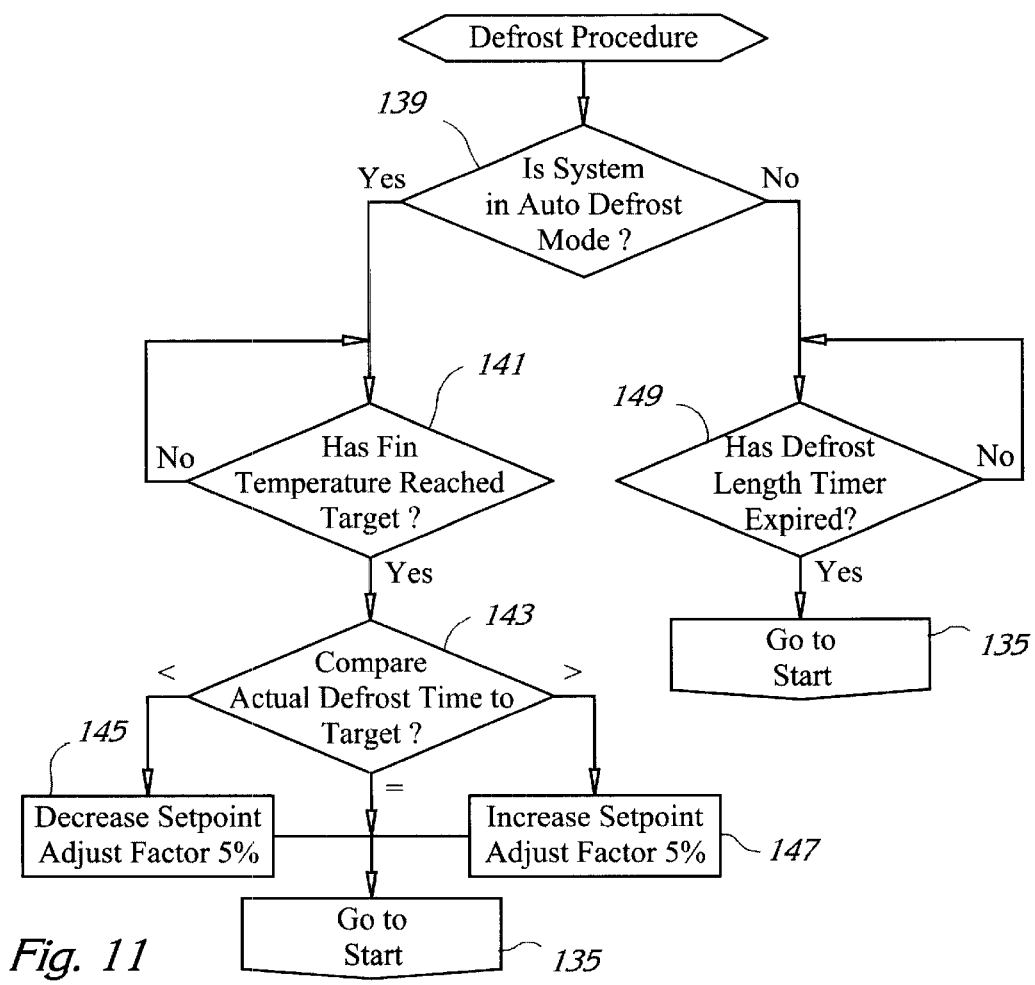
FIG. 11 is a schematic block diagram illustrating the additional steps involved in a preferred embodiment of the invention.

Referring to FIG. 11, a schematic block diagram of the software program that operates a preferred embodiment of the invention is presented. The software program executes additional steps in the above technique for operating a refrigeration system. If a defrost cycle has been initiated in defrost step 115 and execution of second mode determination step 139 indicates that the system is in an auto defrost mode, fin temperature comparison step 141 is executed which involves determining whether the fin temperature has reached a fin temperature target that has been entered via user input on the front panel of controller. If the fin temperature has reached the fin temperature target, defrost time comparison step 143 is implemented which involves comparing the actual defrost time to the target defrost time that has been entered via user input on the front panel of the controller. The left side of the decision node executes if the actual defrost time is less than the target value; the right side of the node executes if the actual defrost time is greater than the target value. Thus, if the actual defrost time is less than the target defrost time, decrease adjust factor step 145 is executed which involves decreasing the setpoint adjust factor, preferably by about five percent and executing go-to-start step 135. If the actual defrost time is greater than the target defrost time, increase adjust factor step 147 is executed which involves increasing the setpoint adjust factor, preferably by about five percent and executing go to start step 135. If the system is not in the auto defrost mode, defrost time comparison step 149 is executed which involves determining whether the time until defrost has expired. If the time until defrost has expired, go-to-start step 135 is executed.

WORKING EXAMPLE

Testing of a prototype of frost sensor 11 was performed in a walk-in cooler/freezer. The test facility included a walk-in refrigerated room, a data-acquisition system, the data-acquisition and control software, a humidification system, and a complete refrigeration system with both electric and hot-gas defrost evaporative coils. The test facility was automated to allow a large number of tests to be conducted with a minimum of labor.

The dimensions of the refrigerated room used in the testing program were 10 feet by 10 feet by 10 feet. It was framed with 2-inch by 4-inch studs, drywalled on the inside and insulated to R-16 with a vapor barrier on the outside. A drain was provided in the floor, through which the ice melted during the defrost cycle was removed.

Two evaporative coils were located inside the refrigerated room on a cart. The top coil was an electric-defrost coil, and the bottom coil was a hot-gas defrost coil. Only one of the coils was used in any given test. Solenoid valves controlled by the data-acquisition system were used to control which coil was active for the test. These two types of coils were chosen because they are representative of the two largest classes of evaporative coils. Both coils had a multi-pass design and six fins per inch. The fins on both coils were corrugated, with the electric-defrost coil having significantly deeper corrugations. The fins on both coils were made of aluminum.

The piping from the evaporative coils ran through the wall of the refrigerated room to the rest of the refrigeration system. The rest of the refrigeration system was mounted on a wooden base and consists of a ¾-HP compressor, a condenser, and appropriate control circuits.

In summary, the test facility prepared was representative of a large class of refrigeration systems in which frost sensor 11 is expected to operate. The facility used a complete refrigeration system in a configuration that is a realistic representation of an actual field site. The system was highly automated to allow rapid testing with minimal labor, while allowing collection of a large set of data for analysis. Tests were run under high and low humidity conditions.

Figure 12:
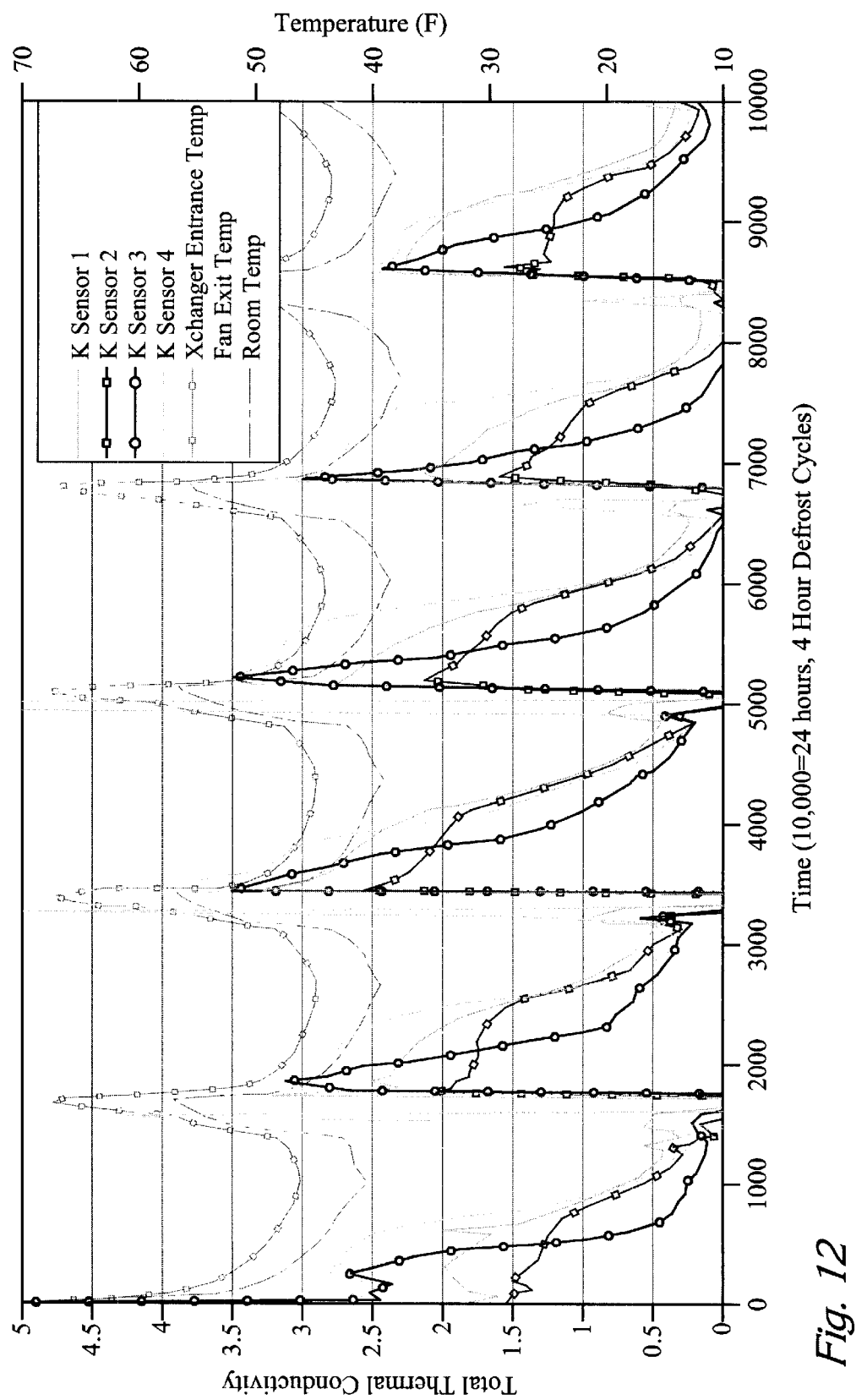
FIG. 12 is a graph of data collected during testing of a prototype of a preferred embodiment of the invention.

Data collected with multiple frost sensors 11 and other indicated sensors are presented in FIG. 12. The tests showed that the signals produced by frost sensors 11 correctly determined the level of frost. The tests showed that reliance on the proposed control signal (K) was successful under a variety of humidity conditions, under a variety of thermostat settings for the room temperature, under a variety of loads (simulated with a trough of warm water filled or emptied), with doors opening and closing, and with doors being left ajar or wide open.

Many variations of the invention will occur to those skilled in the art. Some variations include just a defrost sensor. Other variations use just a heat flux sensor and not the disclosed temperature sensors to calculate K. Yet other variations call for a defrost control system or a refrigeration operating system. All such variations are intended to be within the scope and spirit of the invention.

We claim:

1. A frost sensor for mounting on an evaporative heat exchanger that is exposed to an airflow, said frost sensor comprising:
    a printed circuit board comprising an electrical circuit;
    a first temperature sensor that is mounted on said printed circuit board and that is electrically connected to said electrical circuit;
    a copper clip;
    a heat flux sensor that is mounted on said copper clip and that is electrically connected to said electrical circuit;
    a spring clip that is operative to hold said heat flux sensor or said copper clip and said first temperature sensor against a first cooling fin of said evaporative heat exchanger and to hold a part of said printed circuit board against said first cooling fin on the side of said cooling fin opposite the side against which said heat flux sensor or said copper clip is being held;
    a second temperature sensor that is mounted on said printed circuit board in such a manner that the airflow impinges on the second temperature sensor before it impinges on said first cooling fin; and
    an electrical connector that is mounted on said printed circuit board and electrically connected to said electrical circuit.

2. The frost sensor of claim 1 wherein said heat flux sensor is mounted on said copper clip by means of an adhesive and said copper clip is held against said first cooling fin.

3. The frost sensor of claim 1 further comprising:
    a third temperature sensor that is in thermal contact with said evaporative coil at a location where ice tends to melt the slowest and that is thermally insulated from said airflow.

4. A defrost control system that comprises a controller and an evaporative heat exchanger to which is attached the frost sensor of claim 1.

5. A refrigeration system that comprises a compressor, a condenser and an evaporative heat exchanger to which is attached the frost sensor of claim 1.

6. A device for sensing frost on a cooling fin of an evaporative heat exchanger that is subjected to an airflow, said device comprising:
    a heat flux sensor that is in thermal contact with and located on one side of said fin;
    a thermal insulator that is in thermal contact with said fin and located on the other side of said fin, opposite the location of said heat flux sensor;
    a first temperature sensor that is in contact with said airflow before said airflow is in contact with said fin; and
    a second temperature sensor that is in thermal contact with said fin and that is thermally insulated from said airflow.

7. The device of claim 6 further comprising:
    a third temperature sensor that is in thermal contact with said evaporative heat exchanger at a location where ice tends to melt slower than said ice melts in the vicinity of said fin and that is thermally insulated from said airflow.

8. The device of claim 6 wherein said heat flux sensor is a differential thermopile.

9. The device of claim 6 in which said thermal insulator is at least a portion of a printed circuit board.

10. A sensor for characterizing the heat-transfer effectiveness of an evaporative coil that comprises a plurality of cooling fins that are subject to insulating accumulations, said sensor comprising:
    means for measuring the heat flow from an airflow to a first cooling fin that produces a first signal;
    means for measuring the temperature of said first cooling fin that produces a second signal; and
    means for measuring the temperature of said airflow that produces a third signal;
    wherein said three signals are used to quantify the total thermal conductivity of said accumulations.

11. The sensor of claim 10 wherein said third signal is used to determine when said coil has been adequately defrosted during a defrost cycle.

12. The sensor of claim 10 further comprising:
means for scheduling the defrost cycle for said evaporative coil.

13. The sensor of claim 10 further comprising:
means for measuring the temperature of a second cooling fin that produces a fourth signal, said second cooling fin being located where ice tends to melt more slowly than it does on said first cooling fin during a defrost cycle.

14. The sensor of claim 12 wherein said fourth signal is used to determine when said coil has been adequately defrosted during a defrost cycle.

15. A method for defrosting a refrigeration system that includes an evaporative heat exchanger having a fin that is exposed to an airflow and that is subject to an insulating accumulation, said method comprising:
measuring the heat flux from the airflow into the fin, the temperature of the fin and the temperature of the airflow;
calculating the total thermal conductivity or total thermal resistance value of said insulating accumulation; and
initiating a defrost cycle when the total thermal conductivity or total thermal resistance value reaches a setpoint.

16. The method of claim 15 further comprising:
terminating said defrost cycle when the temperature of the fin reaches a target temperature.

17. The method of claim 15 further comprising:
comparing heat flux data collected at a previous time with heat flux data collected at a subsequent time; and
initiating an alarm procedure if the comparison indicates that the measured heat flux is trending downward.

18. A technique for operating a refrigeration system that includes an evaporative heat exchanger having a fin that is exposed to an airflow and that is subject to an insulating accumulation, said technique comprising:
measuring the heat flux from the airflow into the fin, the temperature of the fin and the temperature of the airflow;
determining whether the heat flux is below an expected value;
if the heat flux is not below the expected value, calculating the total thermal conductivity or total thermal resistance value of said insulating accumulation and applying a setpoint adjustment factor;
resetting the system timers;
determining whether the system is in an auto defrost mode;
if the system is in an auto defrost mode, determining whether the heat flux or the or the total thermal conductivity or total thermal resistance value has reached a setpoint;
if the system is not in an auto defrost mode, determining whether the time until defrost has expired; and
if either the heat flux or the total thermal conductivity or total thermal resistance value has reached a setpoint or the time until defrost has expired, initiating a defrost cycle.

19. The technique of claim 18 further comprising:
if the heat flux is below the expected value, determining if the heat flux is downward trending;
if the heat flux is downward trending, concluding that an evaporator dirt accumulation is indicated, sending an evaporator dirt accumulation alarm message and setting the system to a timer mode; and
if the heat flux is not downward trending, concluding that an equipment failure is indicated, sending an equipment failure alarm message and setting the system to a time mode.

20. The technique of claim 18 further comprising:
if a defrost cycle has been initiated and the system is in an auto defrost mode, determining whether the fin temperature has reached a fin temperature target;
if the fin temperature has reached the fin temperature target, comparing the actual defrost time to the target defrost time;
if the actual defrost time is less than the target defrost time, decreasing the setpoint adjust factor;
if the actual defrost time is greater than the target defrost time, increasing the setpoint adjust factor; and
if the system is not in the auto defrost mode, determining whether the time until defrost has expired.

21. A process for control of frost in a system that transfers heat from air to a refrigerant along a thermal path that passes through a surface of a fin, said process comprising:
measuring the thermal conductivity of the thermal path from the air into a single portion of the surface of the fin by means of a sensor that is capable of measuring the heat flux from said air into the single portion of the surface;
recognizing a reduction in thermal conductivity due to the thermal insulation effect of the frost and due to the loss of airflow from excessive ice formation; and controlling the defrosting of the system.

22. A refrigeration system comprising a compressor, a condenser and an evaporative heat exchanger, said system being operated in accordance with the process of claim 21.

23. A method for defrosting a refrigeration system that includes an evaporative heat exchanger having a fin with a surface that is exposed to an airflow and that is subject to an insulating accumulation, said method comprising:
measuring the heat flux from the airflow essentially perpendicularly into the surface of the fin;
calculating the thermal conductivity or thermal resistance value of said insulating accumulation; and
initiating a defrost cycle when the thermal conductivity or total thermal resistance value reaches a setpoint.

24. A device for sensing frost on a cooling fin of an evaporative heat exchanger that is exposed to an airflow, said device comprising:
a heat flux sensor having a side that is exposed to said airflow and another side that is in thermal contact with a first portion of said fin and being configured to measure the heat flow from said airflow essentially perpendicularly into said first portion of said fin.

25. The device of claim 24 wherein the temperature of said side exposed to said airflow does not differ from the temperature of a second portion of said fin adjacent to said heat flux sensor by more than about three degrees Fahrenheit.

26. A method for defrosting a refrigeration system that includes an evaporative heat exchanger having a fin with a surface that is exposed to an airflow and that is subject to an insulating accumulation, said fin having attached thereto a heat flux sensor, said method comprising:

measuring the rate at which heat is flowing from the airflow along a path that passes through any insulating accumulation, through the heat flux sensor and into the surface of the fin;

calculating the thermal conductivity or thermal resistance value of any insulating accumulation; and initiating a defrost cycle when the thermal conductivity or total thermal resistance value reaches a setpoint.

27. A device for sensing frost on a cooling fin of an evaporative heat exchanger that is exposed to an airflow, said device comprising:

a heat flux sensor having a side that is exposed to said airflow and another side that is in thermal contact with a first portion of said fin, said heat flux sensor being configured to measure the heat flow from said airflow through said heat flux sensor and into said first portion of said fin.

28. A device for sensing frost on a cooling fin of an evaporative heat exchanger that is exposed to an airflow, said device comprising:

a heat flux sensor having a side that is exposed to said airflow and another side that is in thermal contact with a first portion of said fin, said heat flux sensor being comprised of a thin film with hot junctions being spread over one of said sides and cold junctions being spread over the other of said sides to measure the heat flow from said airflow through said heat flux sensor and into said first portion of said fin.

* * * * *